US010123880B2

(12) United States Patent
Chen (10) Patent No.: US 10,123,880 B2
(45) Date of Patent: Nov. 13, 2018

(54) EXPANDABLE SPINAL INTERBODY DEVICE (71) Applicant: Ossaware Biotech Co., Ltd., Changhua Hsien (TW)

(72) Inventor: Kuei Jung Chen, Changhua Hsien (TW)

(73) Assignee: OSSAWARE BIOTECH CO., LTD., Changhua Hsien (TW)

( * ) Notice: Subject to any disclaimer, the term of this patent is extended or adjusted under 35 U.S.C. 154(b) by 488 days.

(21) Appl. No.: 14/792,752

(22) Filed: Jul. 7, 2015

(65) Prior Publication Data

US 2016/0022428 A1     Jan. 28, 2016

(30) Foreign Application Priority Data

Jul. 22, 2014   (TW) ............................. 103125170 A (51) Int. Cl.
| | |
|---|---|
| A61F 2/44 | (2006.01) |
| A61F 2/46 | (2006.01) |
| A61F 2/30 | (2006.01) |

(52) U.S. Cl.
CPC ............ *A61F 2/442* (2013.01); *A61F 2/4425* (2013.01); *A61F 2/4455* (2013.01); *A61F 2/4611* (2013.01); *A61F 2002/30014* (2013.01); *A61F 2002/30131* (2013.01); *A61F 2002/30471* (2013.01); *A61F 2002/30565* (2013.01); *A61F 2002/30566* (2013.01); *A61F 2002/30593* (2013.01); *A61F 2002/4629* (2013.01); *A61F 2230/0063* (2013.01)

(58) Field of Classification Search
CPC ............................. A61F 2/442; A61F 2/4425
See application file for complete search history.

(56) References Cited

U.S. PATENT DOCUMENTS

| | | | |
|---|---|---|---|
| 5,865,848 A | 2/1999 | Baker | |
| 5,888,227 A | 3/1999 | Cottle | |
| 5,989,289 A | 11/1999 | Coates et al. | |
| 6,139,579 A | 10/2000 | Steffee et al. | |
| 6,511,509 B1 | 1/2003 | Ford et al. | |
| 8,241,358 B2 | 8/2012 | Butler et al. | |
| 2005/0043800 A1 | 2/2005 | Paul et al. | |
| 2005/0113920 A1 | 5/2005 | Foley et al. | |
| 2006/0142858 A1 | 6/2006 | Colleran et al. | |
| 2006/0224241 A1 | 10/2006 | Butler et al. | |
| 2013/0079883 A1* | 3/2013 | Butler | A61F 2/4425 623/17.16 |
| 2013/0144391 A1* | 6/2013 | Siegal | A61F 2/442 623/17.16 |

* cited by examiner

*Primary Examiner* — Zade Coley
*Assistant Examiner* — Olivia C Chang
(74) *Attorney, Agent, or Firm* — Leong C. Lei (57) ABSTRACT

A bone graft or spinal interbody device includes a frame member having two end segments for forming a chamber in the frame member, and two arms each include an outer end portion hinged to the outer end portion of the end segments of the frame member, and the inner end portions of the arms are hinged together for allowing the arms to be pivoted toward the frame member at an innermost folding position or away from the frame member to an outermost working position, and the arms are sprung away from the frame member to the outermost working position when the arms are pushed away from the frame member for a selected distance to an inner dead center (D).

10 Claims, 9 Drawing Sheets

EXPANDABLE SPINAL INTERBODY DEVICE

BACKGROUND OF THE INVENTION

1. Field of the Invention

The present invention relates to a bone graft or spinal interbody device, and more particularly to a radially expandable bone graft or spinal interbody device, interbody device, spinal prosthesis, or the like including three hinged members or elements hinged and coupled together and including an improved structure or configuration for allowing the hinged members or elements to be easily and quickly expanded and/or to be easily and quickly contracted.

2. Description of the Prior Art

Typical bone grafts, intervertebral implants, intervertebral spacers, bone graft devices or the like have been developed and provided for being filled or fitted or engaged into the bone materials or members of the human or user for repairing bone defects, such as the damaged or degenerated spinal disc in a spinal column or vertebrae of a human or user, or the like, and normally comprise a constructed or spatial member for engaging into the bone materials or members of the user and for repairing bone defects.

The other radially expandable interbody devices, spinal prosthesis or the like are configured to be delivered to an implant site in a radially collapsed state or with radially minimal dimensions and then radially expanded or with radially maximum dimensions at the implant site hence the term expandable or dynamic. In this manner, the radially expandable interbody device may be delivered to the implant site through a small delivery area when in the radially collapsed state and then easily radially expanded when implanted. The radially expandable interbody device may be fashioned from a biocompatible material such as titanium, a titanium alloy, stainless steel, other metal, polymer, composite, ceramic and/or any combination thereof. The radially expandable interbody device is preferably, but not necessarily, used as a lumbar interbody device and/or for use in an ALIF surgery.

For example, U.S. Pat. No. 5,865,848 to Baker, U.S. Pat. No. 5,888,227 to Cottle, U.S. Pat. No. 5,989,289 to Coates et al., U.S. Pat. No. 6,139,579 to Steffee et al., and U.S. Pat. No. 6,511,509 to Ford et al. disclose several of the typical bone grafts, intervertebral implants, intervertebral spacers, bone graft devices or the like and each also comprising a constructed or spatial member, such as an artificial spinal disc prosthesis, or the like for fitting or engaging into the bone materials or members, such as the damaged or degenerated spinal column or vertebrae or spinal disc of the human or user.

However, the conventional or typical bone grafts, intervertebral implants, intervertebral spacers, bone graft devices or the like comprise a constructed or spatial member that includes a solid and stable structure and that may include a great hardness that the bone materials or members of the user may be worn out or damaged or degenerated by the conventional or typical bone grafts, intervertebral implants, intervertebral spacers, bone graft devices or the like after use.

U.S. Patent Application Publication No. 2005/0043800 to Paul et al., U.S. Patent Application Publication No. 2005/0113920 to Foley et al., U.S. Patent Application Publication No. 2006/0142858 to Colleran et al., U.S. Patent Application Publication No. 2006/0224241 to Butler et al., U.S. Patent Application Publication No. 2013/0079883 to Butler et al., and U.S. Pat. No. 8,241,358 to Butler et al. disclose several of the typical radially expandable interbody devices, spinal prosthesis or the like each comprising two or more legs or arms or limbs pivotally coupled together and radially expandable with a driving tool.

However, the pivotally coupled limbs should be expanded with the driving tool and may not be easily and quickly opened or expanded or contracted.

The present invention has arisen to mitigate and/or obviate the afore-described disadvantages of the conventional bone graft or spinal interbody devices.

SUMMARY OF THE INVENTION

The primary objective of the present invention is to provide a radially expandable bone graft or spinal interbody device, interbody device, spinal prosthesis, or the like including three hinged members or elements hinged and coupled together and including an improved structure or configuration for allowing the hinged members or elements to be easily and quickly expanded and/or to be easily and quickly contracted.

The other objective of the present invention is to provide a radially expandable bone graft or spinal interbody device, interbody device, spinal prosthesis, or the like including an expandable and foldable structure or configuration for allowing the spinal interbody device to be easily and quickly engaged into the patient with a reduced or decreased wound or cut.

In accordance with one aspect of the invention, there is provided a spinal interbody device comprising a frame member including two end segments for forming a chamber in the frame member, and the end segments each including an outer end portion, and two arms each including an outer end portion hinged and coupled to the outer end portion of the end segments of the frame member respectively, and the arms each including an inner end portion, and the inner end portions of the arms being hinged and coupled together and arranged for allowing the arms to be pivoted toward and engaged with the frame member at an innermost folding position, and to be pivoted and moved away from the frame member to an outermost working position, and the arms being arranged to be pivoted and sprung away from the frame member to the outermost working position when the arms are pushed and moved away from the frame member for a selected distance (A) to an inner dead center (D).

The inner end portions of the arms are hinged and coupled together at a hinged knot. The hinged knot of the arms is located close to and in contact with the frame member.

The frame member includes a screw hole formed therein for engaging with a mandrel of a driving tool. The frame member includes at least one serrated outer surface formed and provided thereon. The arms each include at least one serrated outer surface formed and provided thereon.

The arms are arranged to be pivoted and sprung toward the frame member to the innermost folding position when the arms are pushed and moved from the outermost working position toward the frame member for a selected distance (B) to an outer dead center (d).

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Referring to the drawings, and initially to FIGS. 1-5, a radially expandable bone graft or spinal interbody device 1 in accordance with the present invention is generally provided for being filled or fitted or engaged into the damaged or degenerated bone materials or members 80, such as the mandible, the spinal column 80 or vertebrae of a human or user (FIGS. 7-9), or the like for repairing bone defects, for example, the spinal interbody device 1 may be directly engaged into the damaged or degenerated portion of the mandible, or may be disposed or attached or mounted or secured or engaged into the space between two vertebral bodies 80 (FIGS. 7-9) for forming or acting as the intervertebral disk and for sustain the vertebral bodies 80 in place.

For example, the spinal interbody device 1 comprises a constructed or three dimensional or spatial or arched or curved or L-shaped body or frame member 10 including a base area or body segment or portion 11 and two end portions or segments 12, 13 formed integral as a one-piece structure or configuration, for forming or defining a recess or depression or chamber 14 in the frame member 10, and the end segments 12, 13 each include a distal or outer end portion 15, 16 hinged or pivotally coupled to the hinged members or elements or bars or legs or limbs or arms 20, 30 respectively, for example, the arms 20, 30 each include an outer end portion 21, 31 hinged or pivotally coupled to the outer end portion 15, 16 of the end segments 12, 13 at an outer hinged point or knot 36, 37 respectively (FIG. 3), and each include an L-shaped or curved inner end portion 22, 32. Either or both of the frame member 10 and the arms 20, 30 include a deformable or elastic characteristic.

Figure 1:
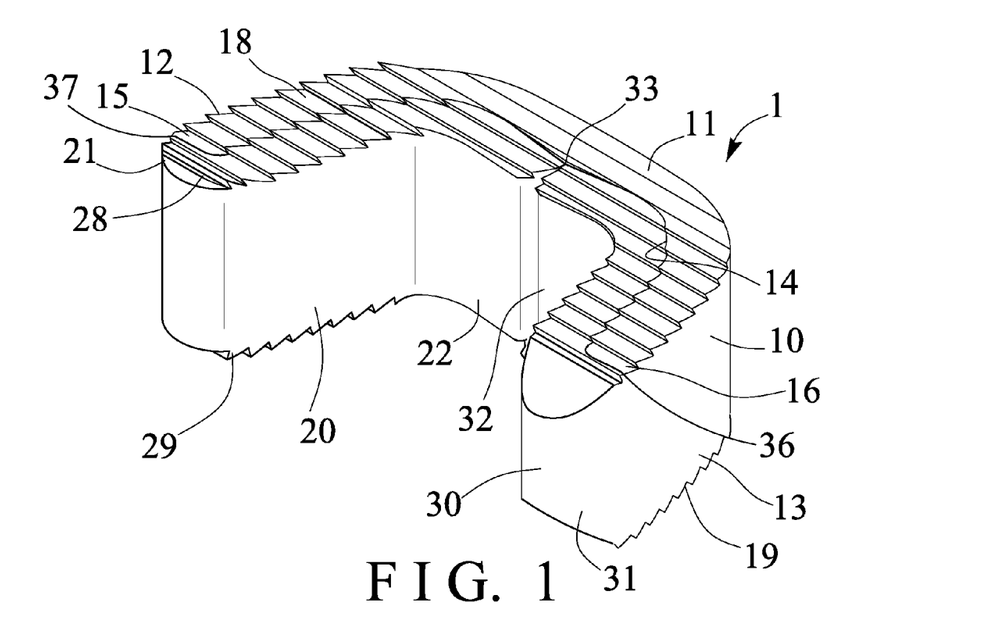
FIG. 1 is a perspective view of a radially expandable bone graft or spinal interbody device in accordance with the present invention, for fitting or engaging into the bone materials or members of the user.
Figure 2:
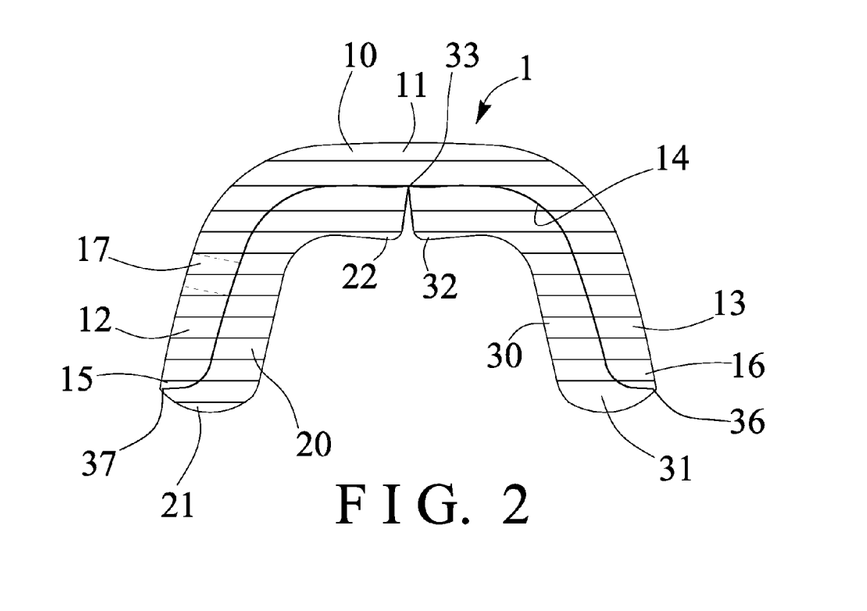
FIG. 2 is a top plan schematic view of the radially expandable bone graft or spinal interbody device.
Figure 3:
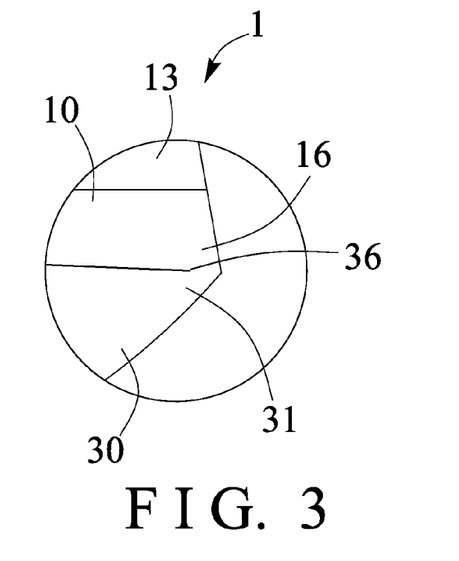
FIGS. 3 and 4 are enlarged partial plan schematic views of the radially expandable bone graft or spinal interbody device.
Figure 4:
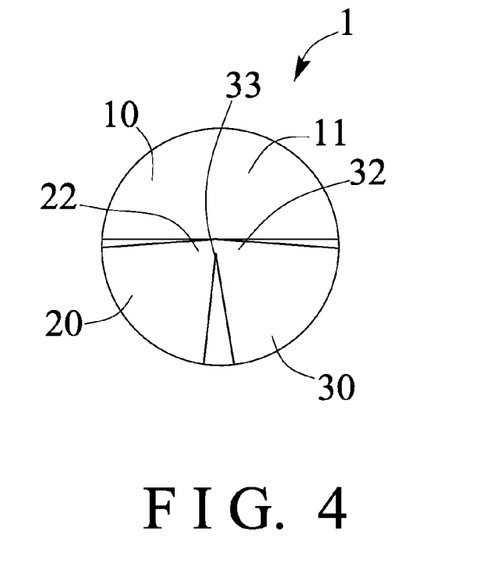
Figure 5:
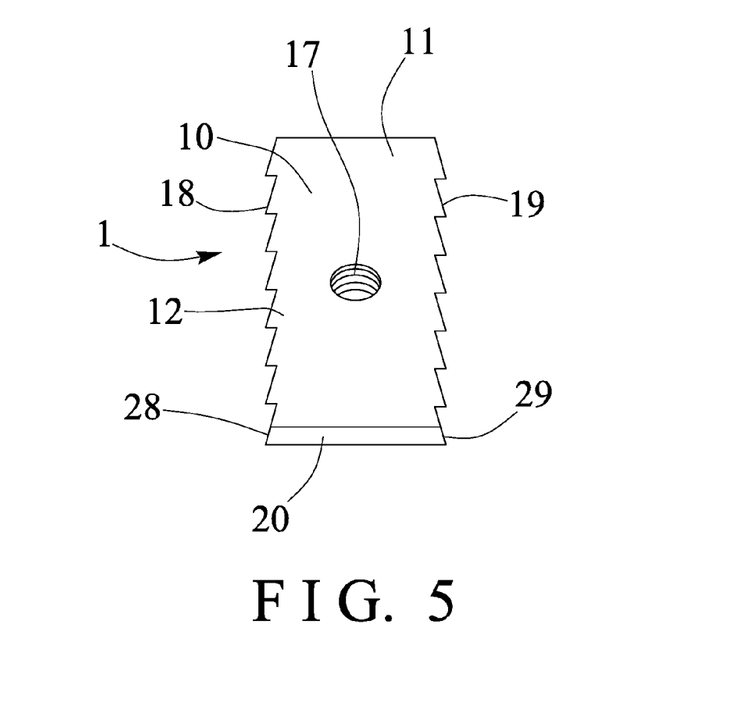
FIG. 5 is a side plan schematic view of the radially expandable bone graft or spinal interbody device.
Figure 6:
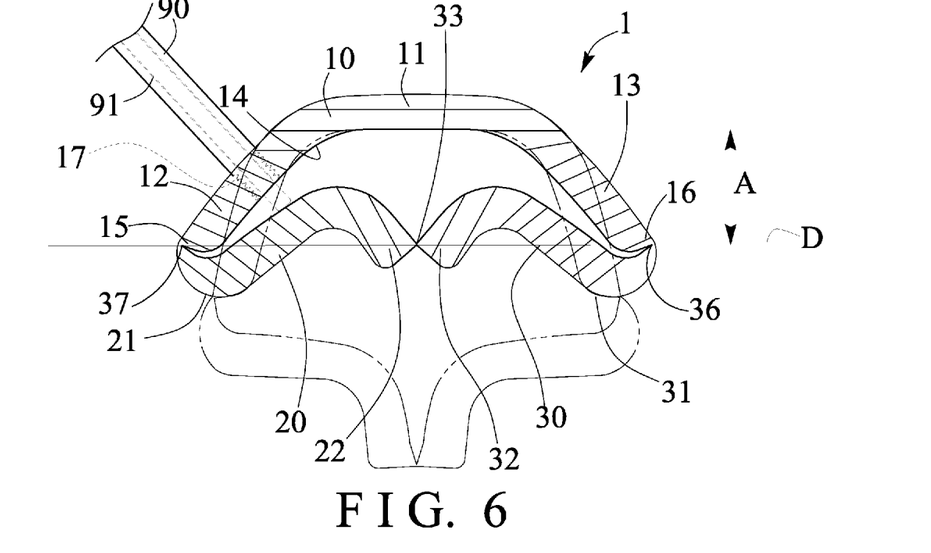
FIG. 6 is another top plan schematic view similar to FIG. 2, illustrating the operation of the radially expandable spinal interbody device.

As shown in FIGS. 1, 2 and 4, the inner end portions 22, 32 of the arms 20, 30 are hinged or pivotally coupled together at an inner hinged point or knot 33, and arranged for allowing the arms 20, 30 to be pivoted or moved toward or contacted or engaged with the frame member 10 when the arms 20, 30 are engaged into the chamber 14 of the frame member 10 (FIGS. 1, 2), where the hinged knot 33 of the arms 20, 30 are arranged or located close to or in contact with the base portion 11 of the frame member 10 (FIG. 4). It is preferable that the frame member 10 and the arms 20, 30 and the hinged knots 33, 36, 37 are formed integral as one-piece structure. As shown in FIGS. 2, 5 and 6, the frame member 10 includes a screw hole 17 formed therein, such as formed in the base portion 11 or in one of the end segments 12, 13 of the frame member 10 for threading or engaging with a mandrel 91 of a driving tool 90 (FIGS. 6-8).

Figure 7:
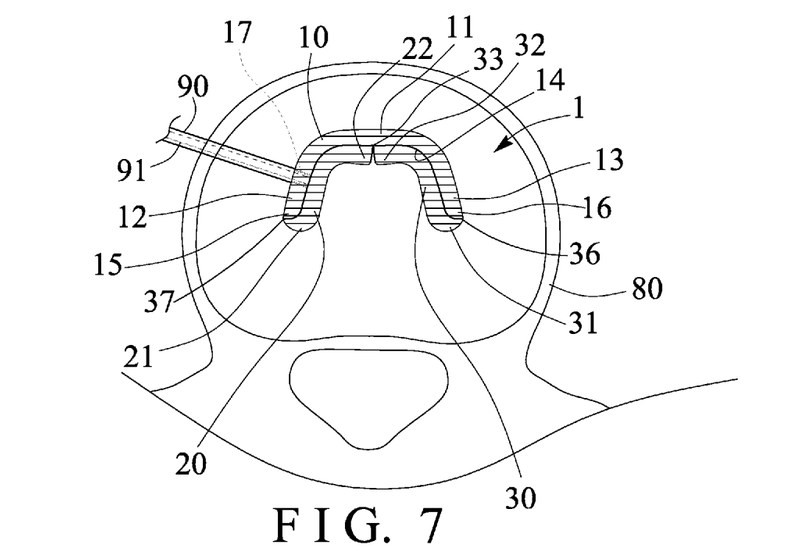
FIGS. 7, 8, 9, 10 are further top plan schematic views similar to FIGS. 2, 6, illustrating the operation of the radially expandable spinal interbody device.
Figure 8:
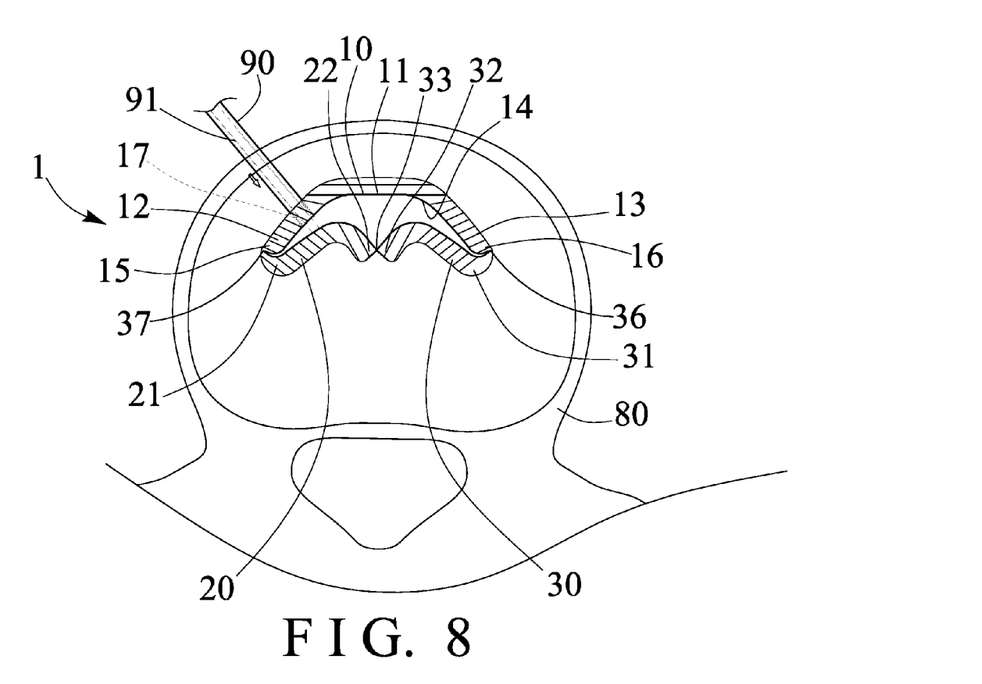
Figure 9:
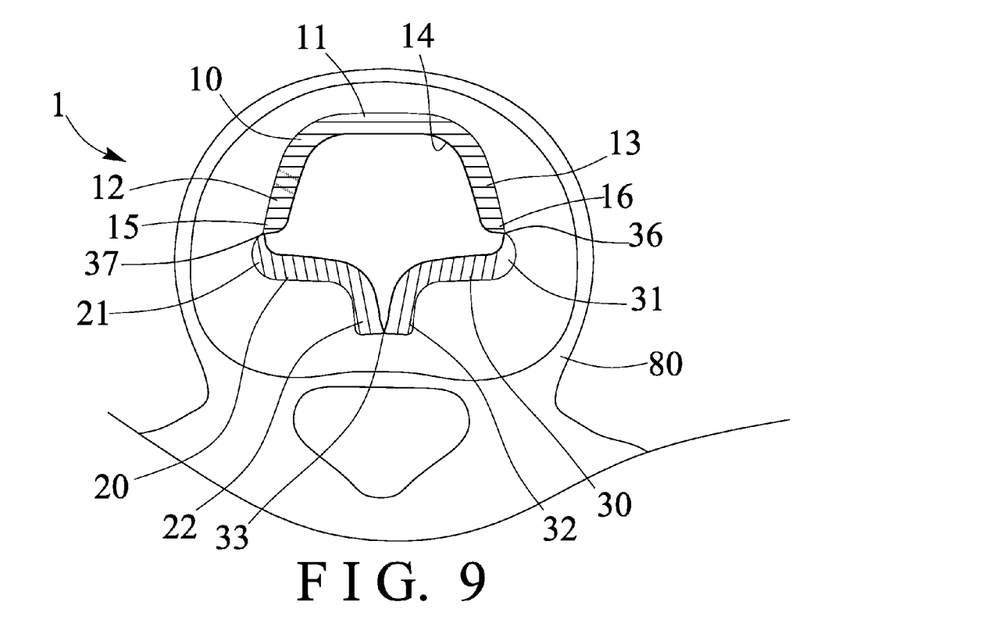

In operation, as shown in FIGS. 7-10, the spinal interbody device 1 may be engaged into the damaged or degenerated portion of the mandible, or may be disposed or attached or mounted or secured or engaged into the space between two adjacent vertebral bodies 80, and the mandrel 91 of the driving tool 90 may be threaded or meshed or engaged with the screw hole 17 of the frame member 10 (FIGS. 6-8), and may be in contact with either of the arms 20, 30 for selectively pushing and moving and disengaging or separating the arms 20, 30 from the frame member 10, and arranged for allowing the arms 20, 30 to be pivoted or moved and sprung away from the frame member 10 to the outermost or working position as shown in FIG. 9, automatically when the arms 20, 30 are pushed and moved away from the frame member 10 for a selected distance (A) to an inner dead center (D, FIGS. 6, 8) where the hinged knot 33 of the arms 20, 30 is in line with and located between the hinged knots 36, 37 of the arms 20, 30 and the frame member 10.

Figure 10:
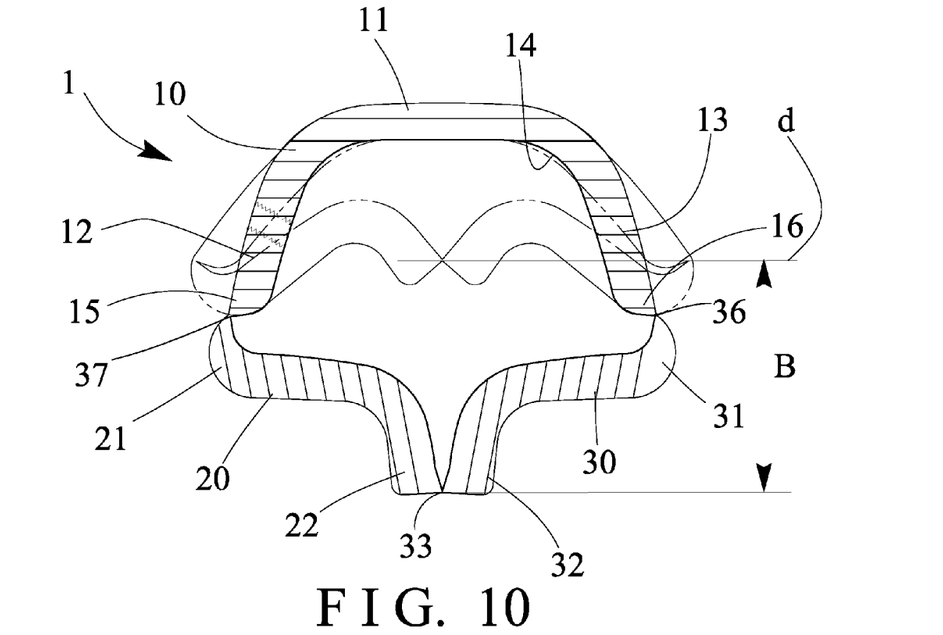
Figure 11:
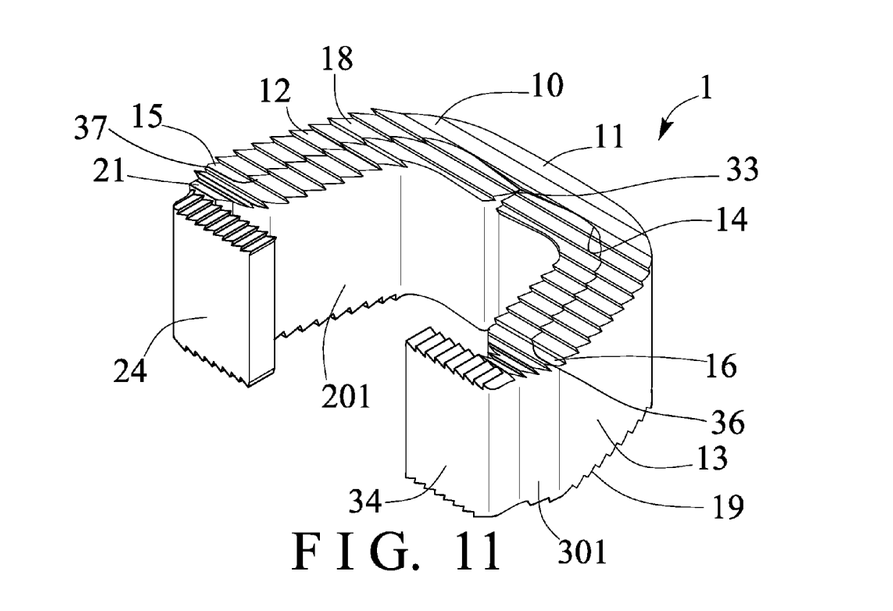
FIG. 11 is another perspective view similar to FIG. 1, illustrating the other arrangement of the radially expandable spinal interbody device.
Figure 12:
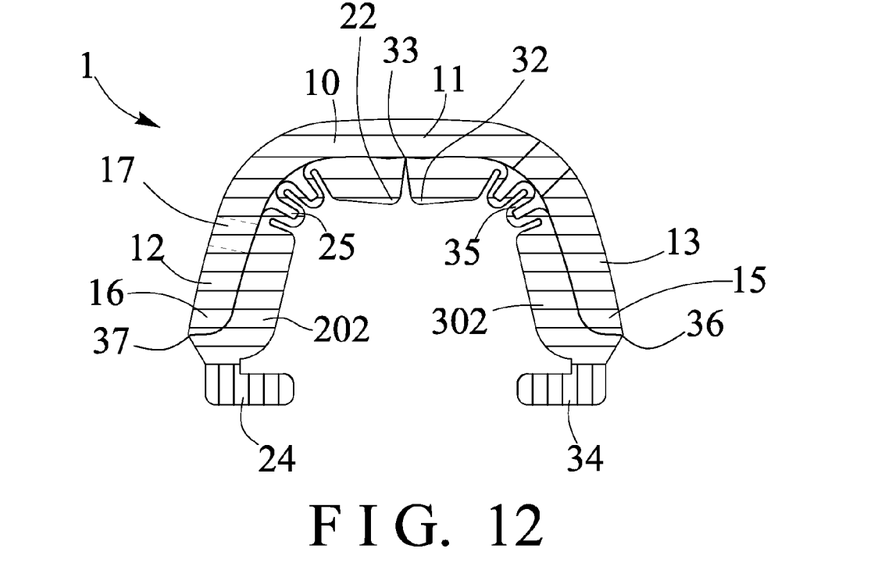
FIG. 12 is a still further top plan schematic view similar to FIGS. 2, 6, illustrating the further arrangement of the radially expandable spinal interbody device.
Figure 13:
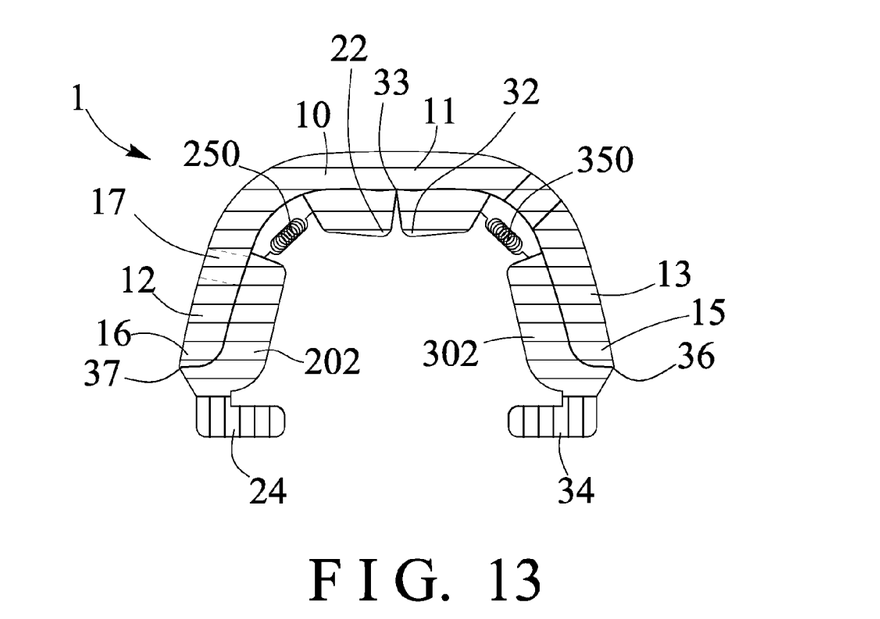
FIG. 13 is a still further top plan schematic view similar to FIG. 12, illustrating the still further arrangement of the radially expandable spinal interbody device.

On the contrary, as shown in FIG. 10, when the arms 20, 30 are pushed and moved from the outermost or working position (FIG. 9) toward the frame member 10 for a selected distance (B) to an outer dead center (d) where the hinged knot 33 of the arms 20, 30 is in line with and located between the hinged knots 36, 37 of the arms 20, 30 and the frame member 10, and the arms 20, 30 are arranged to be pivoted or moved and sprung toward the frame member 10 to the innermost or folding or storing position as shown in FIG. 7, automatically. Alternatively, as shown in FIG. 11, the arms 201, 301 each may include an additional reinforcing member 24, 34 attached thereto or extended therefrom for increasing the contact area of the arms 201, 301. Further alternatively, as shown in FIG. 12, the arms 202, 302 each may include a wavy or corrugated or flexible structure or configuration 25, 35 formed or provided therein for increasing the flexibility of the arms 202, 302; or each may include a spring biasing member 250, 350 formed or provided therein (FIG. 13) for increasing the flexibility of the arms 202, 302 respectively.

It is to be noted that the arms 20, 30 may be pivoted or moved and sprung away from the frame member 10 to the outermost or working position as shown in FIG. 9, automatically when the arms 20, 30 are pushed and moved away from the frame member 10 for a selected distance to an inner dead center (D, FIGS. 6, 8); i.e., the arms 20, 30 are not required to be fully or completely pushed and moved away from the frame member 10 from the innermost or folding or storing position as shown in FIG. 7 to the outermost or working position as shown in FIG. 9; and may be pivoted or moved and sprung toward the frame member 10 from the outermost or working position as shown in FIG. 9 to the innermost or folding or storing position as shown in FIG. 7 when the arms 20, 30 are pushed and moved toward the frame member 10 for a selected distance to an outer dead center (d, FIG. 10).

Figure 14:
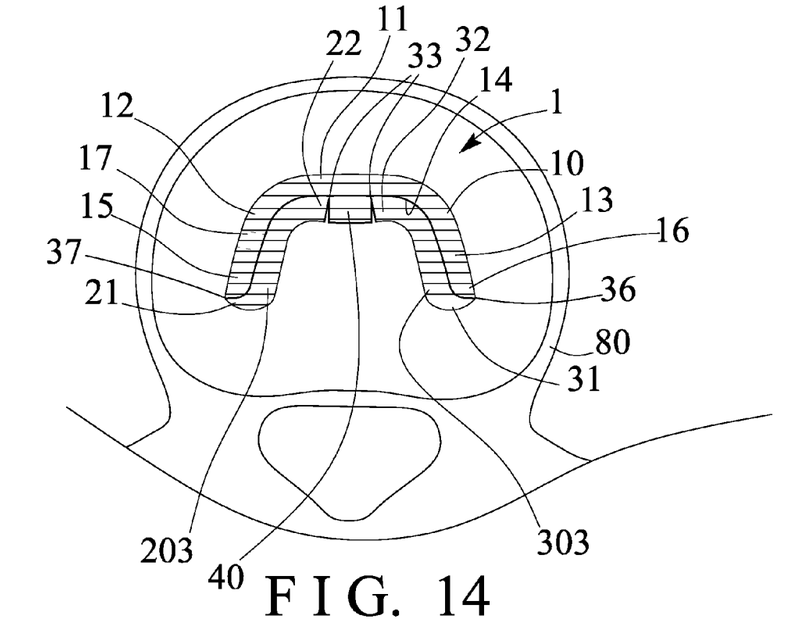
FIGS. 14, 15 are still further top plan schematic views similar to FIGS. 2, 6, 12-13, illustrating the still further arrangement of the radially expandable spinal interbody device.
Figure 15:
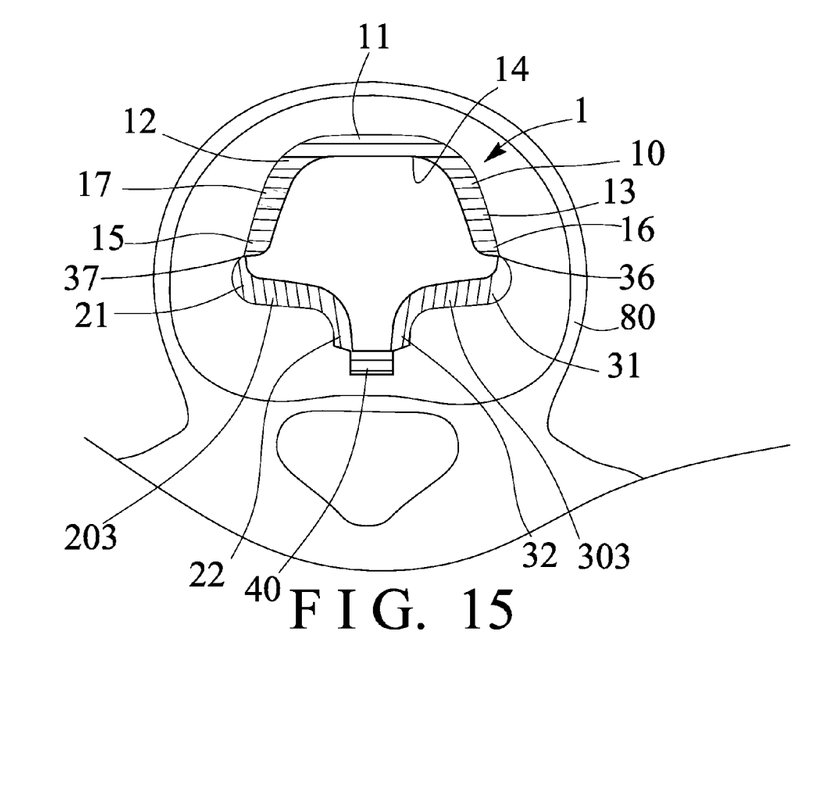
Figure 16:
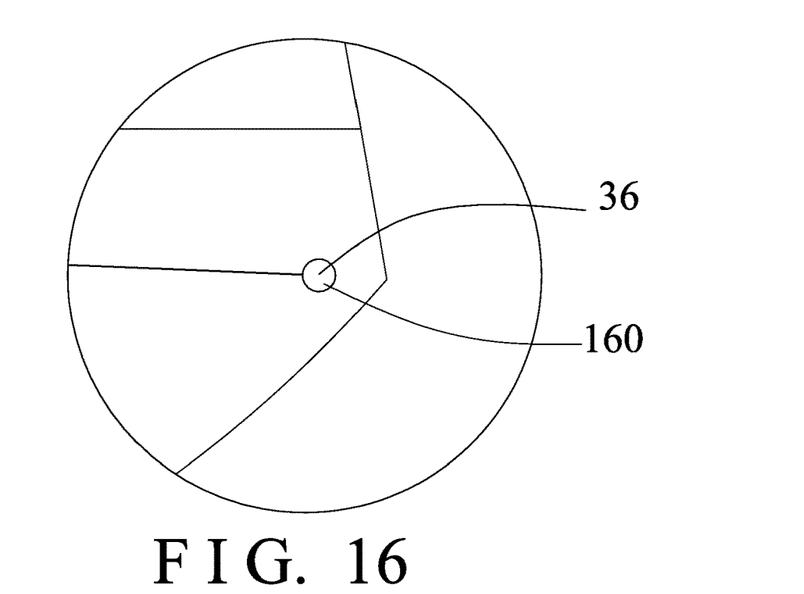
FIGS. 16, 17 are further enlarged partial plan schematic views similar to FIGS. 3 and 4, illustrating the further arrangement of the radially expandable bone graft or spinal interbody device.
Figure 17:
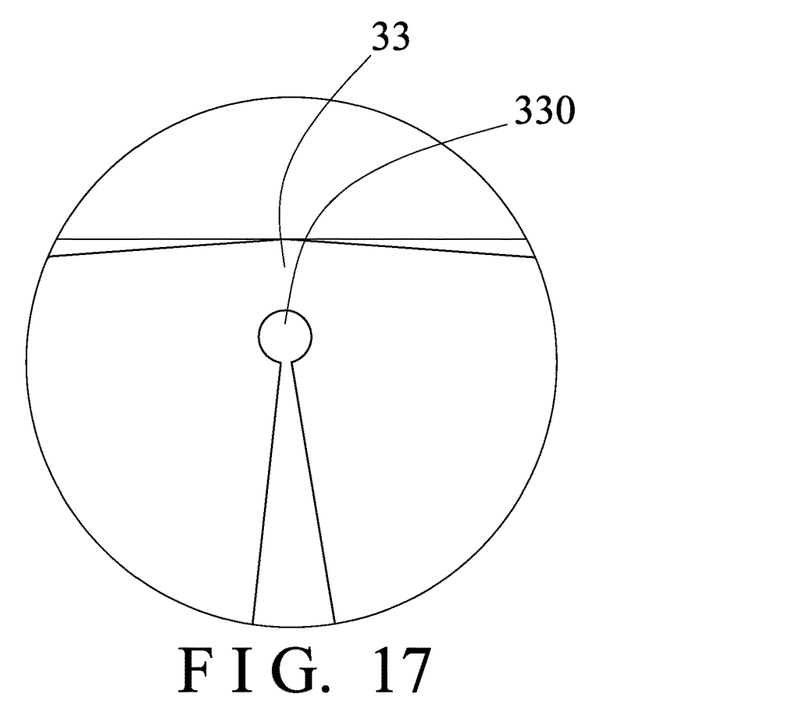

The frame member 10 and/or the arms 20, 30 may include one or more (such as two opposite) serrated or rough outer surfaces 18, 19, 28, 29 formed or provided thereon (FIGS. 1, 5) for increasing the friction with the vertebral bodies 80. Further alternatively, as shown in FIGS. 14, 15, the spinal interbody device 1 may further include an additional arm or hinged member or element or bar or leg or limb 40 hinged or pivotally coupled to and arranged or located between the arms 203, 303 for increasing the flexibility of the arms 203, 303. Further alternatively, as shown in FIG. 16, the outer end portion of the end segment of the frame member and the outer end portion of the arm or the hinged knob 36, 37 includes an opening 160 formed therein, and as shown in FIG. 17, the inner end portions of the arms are hinged or pivotally coupled together at a hinged knot 33, and include an opening 330 formed in the hinged knob 33.

Figure 18:
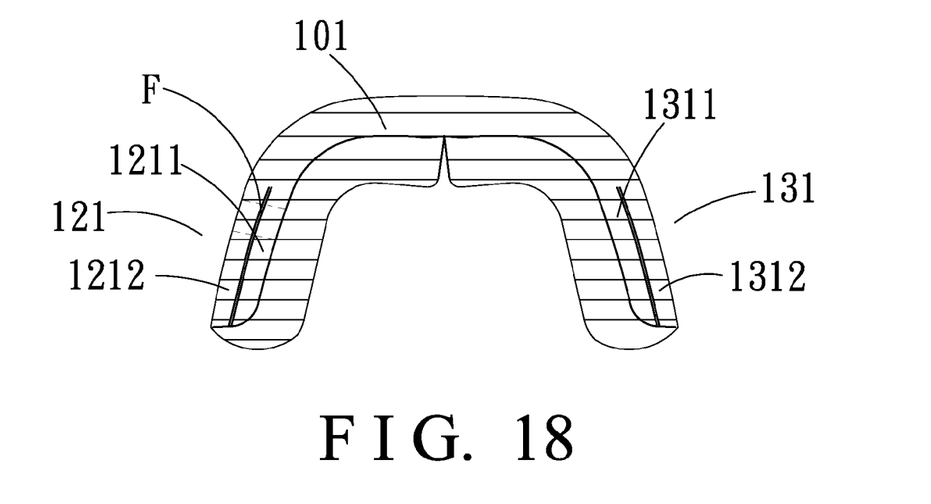
FIG. 18 is a still further top plan schematic view similar to FIGS. 2, 6, 12-13, illustrating the still further arrangement of the radially expandable spinal interbody device.
Figure 19:
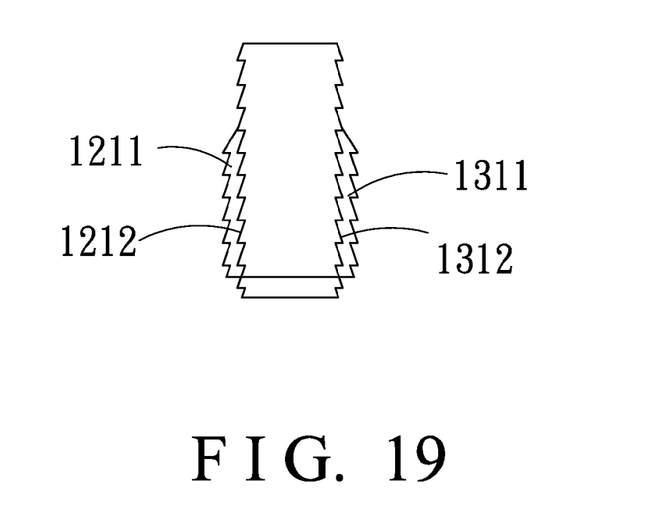
FIG. 19 is a side plan schematic view of the radially expandable bone graft or spinal interbody device as shown in FIG. 18.

Further alternatively, as shown in FIGS. 18 and 19, the end segments 121, 131 of the frame member 101 each include a slit (F) formed therein and formed through the end segments 121, 131 for forming or defining an inner limb 1211, 1311 and an outer limb 1212, 1312, and as shown in FIG. 19, the inner limb 1211, 1311 and the outer limb 1212, 1312 are offset from each other, or include different height for effectively engaging with the vertebral bodies 80 and for preventing the spinal interbody device 1 from being disengaged from the vertebral bodies 80.

Accordingly, the spinal interbody device in accordance with the present invention includes a radially expandable bone graft or spinal interbody device, interbody device, spinal prosthesis, or the like including three hinged members or elements hinged and coupled together and including an improved structure or configuration for allowing the hinged members or elements to be easily and quickly expanded and/or to be easily and quickly contracted, and including an expandable and foldable structure or configuration for allowing the spinal interbody device to be easily and quickly engaged into the patient with a reduced or decreased wound or cut.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A spinal interbody device comprising:
a frame member including:
two end segments for forming a chamber in said frame member, and said end segments each including an outer end portion, and
two arms each including an outer end portion hinged and coupled to said outer end portion of said end segments of said frame member respectively to each define an outer joint point, and said arms each including an inner end portion, and said inner end portions of said arms being hinged and coupled together to define an inner joint point and arranged for allowing said arms to be pivoted toward and engaged with said end segments at an innermost folding position, and to be pivoted and moved away from said end segments to an outermost working position,
wherein said arms are arranged to be pivoted and sprung away from said end segments to the outermost working position when said arms are pushed and moved from the innermost folding position away from said end segments for a selected distance to pass through a dead center that is defined as a location where the inner joint point between the arms is in line with the outer joint point between the arms and the end segments, such that the arms automatically move from the dead center to the outermost working position; and
wherein said arms are arranged to be pivoted and sprung toward said end segments to the innermost folding position when said arms are pushed and moved from the outermost working position toward said end segments for a selected distance to pass through the dead center, such that the arms automatically move from the dead center to the innermost folding position.

2. The spinal interbody device as claimed in claim 1, wherein said inner joint point of said arms is located close to said end segments in said innermost folding position.

3. The spinal interbody device as claimed in claim 1, wherein said inner joint point of said arms is in contact with said end segments in said innermost folding position.

4. The spinal interbody device as claimed in claim 1, wherein said arms are formed integral as a one-piece structure at said inner joint point.

5. The spinal interbody device as claimed in claim 1, wherein said frame member includes a screw hole formed therein for engaging with a mandrel of a driving tool.

6. The spinal interbody device as claimed in claim 1, wherein said frame member includes at least one serrated outer surface formed and provided thereon.

7. The spinal interbody device as claimed in claim 1, wherein said arms each include at least one serrated outer surface formed and provided thereon.

8. The spinal interbody device as claimed in claim 1, wherein said outer end portions of said arms are hinged and coupled to said outer end portions of said end segments of said frame member at an outer joint point respectively.

9. The spinal interbody device as claimed in claim 8, wherein said outer end portions of said arms and said end segments of said frame member are formed integral as a one-piece structure at said outer joint point.

10. The spinal interbody device as claimed in claim 1, wherein at least one of said end segments and said arms include an elastic characteristic.

* * * * *